United States Patent [19]

Millard, Jr. et al.

[11] 4,151,837
[45] May 1, 1979

[54] MOUTH GAG WITH UNIVERSAL ADJUSTABILITY TO THE ALVEOLAR ARCH

[76] Inventors: D. Ralph Millard, Jr., 401 Lake Rd., Bay Point, Miami, Fla. 33137; David H. Slepyan, 2509 Sterling Point Dr., Portsmouth, Va. 23703; Jack Nestor, 110 First Terr. San Marino Island, Miami Beach, Fla. 33139

[21] Appl. No.: 773,060

[22] Filed: Feb. 28, 1977

[51] Int. Cl.² ............................................. A61B 1/24
[52] U.S. Cl. ........................................ 128/12; 128/20
[58] Field of Search ..................................... 128/3–14, 128/341–345, 12–20

[56] References Cited

U.S. PATENT DOCUMENTS

| | | | |
|---|---|---|---|
| 404,652 | 6/1889 | Palmer | 128/14 |
| 853,031 | 5/1907 | Prentis | 128/12 |
| 1,319,904 | 10/1919 | Roberts | 128/12 |
| 1,374,984 | 5/1921 | Cameron | 128/13 |
| 1,388,421 | 8/1921 | Forgrave | 128/12 |
| 2,182,390 | 12/1939 | Reardon | 128/12 X |
| 2,947,305 | 8/1960 | Storz | 128/12 |
| 4,024,859 | 5/1977 | Slepyan et al. | 128/12 |

FOREIGN PATENT DOCUMENTS 113349 9/1900 Fed. Rep. of Germany ............. 128/12
187937 10/1966 U.S.S.R. .................................. 128/12

OTHER PUBLICATIONS

V. Mueller Catalogue, 1938, p. 119.

*Primary Examiner*—Dalton L. Truluck
*Attorney, Agent, or Firm*—Erwin M. Barnett

[57] ABSTRACT

A support post of each alveolar retractor, which is adjustably supported in a clamp means terminating each opposite end of a transverse inferior bar of a surgical mouth gag for both axial rotational and sliding movement, has a superior arcuate bar which at its medial end terminates in an upper jaw engaging member and is mounted in the upper end of said post for lateral-medial sliding adjustment to provide increased surgical exposure. Several modifications of the superior arcuate bar provide pivoting of the upper jaw engaging member to insure an optimum fit. Additional modifications of the transverse inferior bar provide mandibular engaging members which coact with the upper jaw engaging members to mount the mouth gag in operative position independently of the tongue retractor, the latter being removably mountable from the front of the transverse inferior bar without disturbing the position of the mouth gag. Curved tooth-contacting portions of the upper jaw and mandibular engaging members have double bevels to provide non-slip engagement between the teeth.

15 Claims, 21 Drawing Figures

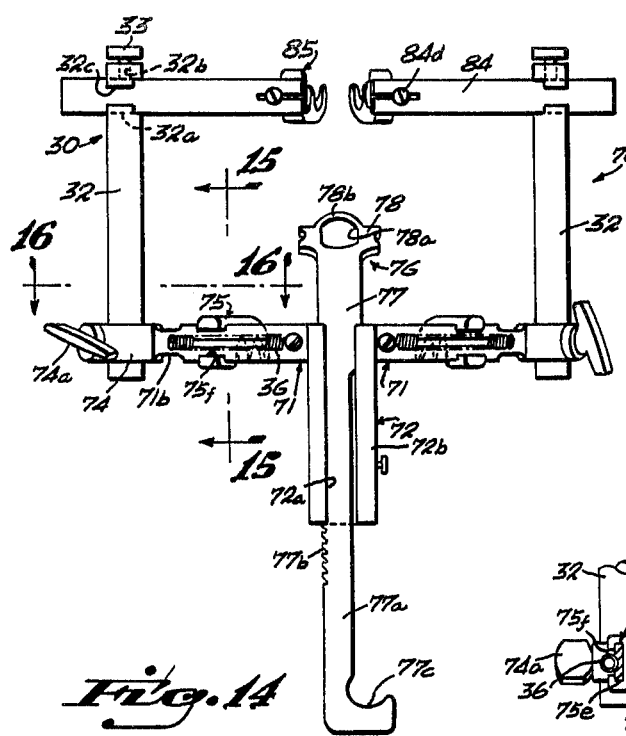
Fig. 14
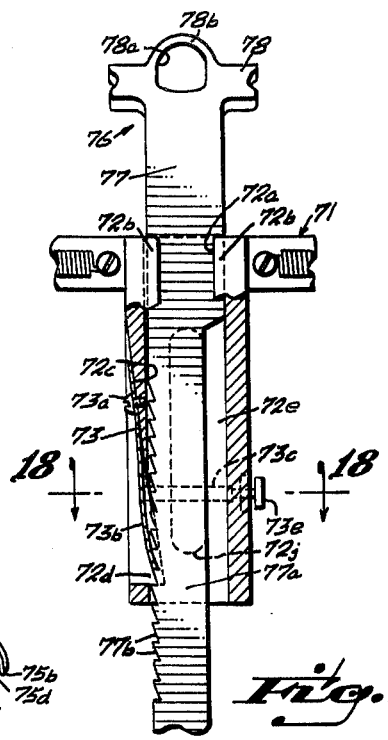
Fig. 17
Fig. 15
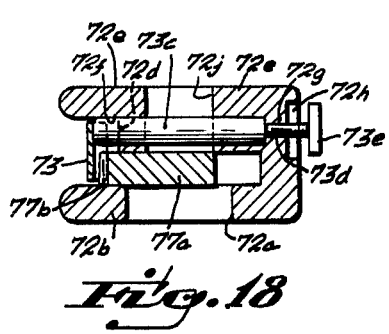
Fig. 18
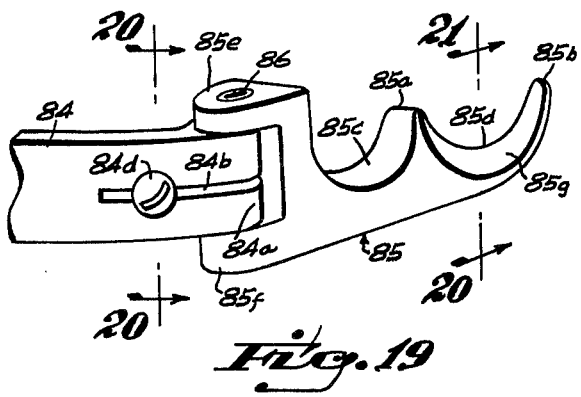
Fig. 19
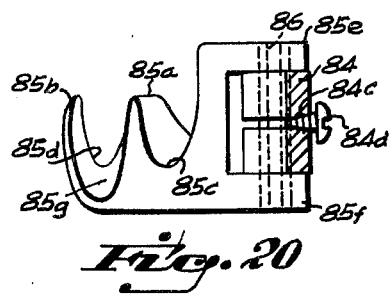
Fig. 20
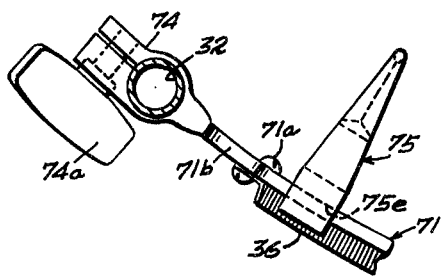
Fig. 16
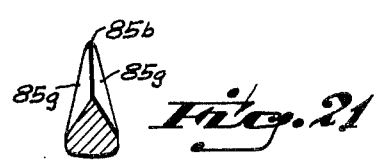
Fig. 21

MOUTH GAG WITH UNIVERSAL ADJUSTABILITY TO THE ALVEOLAR ARCH

BACKGROUND OF THE INVENTION

1. Field of the Invention

This invention relates to surgical instruments and particularly to jaw retractors, also known as mouth gags, for positioning and retaining the jaws in a desired open position during mouth surgery.

2. Description of the Prior Art

This invention is an improvement of the instrument disclosed in U.S Pat. No. 4,024,859 by David H. Slepyan and Jack Nestor entitled Mouth Gag Having Three Dimensional Alveolus Retractor Adjustability.

Whereas the adjustability of the Slepyan and Nestor instrument provides a superior fit and great versatility as compared to the prior Dingman mouth gag, there is a present need for additional surgical exposure accomplished by freedom from supporting elements not actually in use, greater stability in mounting by three point suspension and capability for a balanced, symmetrical two point suspension.

The wide variety of facial configurations presents difficulty encountered by the prior instruments in providing preciseness of fit. This appears to be due to the fixed arcuate shape of the superior support bar and the fixed angle between the latter and its jaw engaging member of the alveolar retractor.

Also, the use of the tongue retractor as the sole lower jaw engaging means has proved to be unreliable, permitting the mouth gag to loosen and shift during surgery and on occasion to be ejected from its properly mounted position. Means for engaging the teeth or gums of the mandible independently of the tongue retractor as well as providing for removably mounting the latter while the mouth gag is being retained in position by coaction between the alveolar and mandibular retractors, as herein provided, will eliminate this problem. The problem of slippage on the teeth by the jaw engaging elements of the alveolar and mandibular retractors is obviated by shaping the contact surfaces for positive engagement between adjacent teeth.

SUMMARY OF THE INVENTION

Among the objects of the invention is to provide jaw retractor instruments having universal adjustability capable of precisely fitting all facial configurations which may be encountered, as for example, maxillary retrusion, collapse or protruding premaxilla, and which will eliminate the disadvantages of prior art devices, meet the needs and achieve the desired results hereinbefore described.

The bilateral alveolar retractors of this mouth gag, as described in the hereinbefore mentioned patent application, comprise lateral support posts which are mounted for both axially slidable and rotatable adjustment in finger actuated clamps terminating opposite ends of the inferior transverse bar which also medially mounts the tongue retractor. The embodiment of the invention provides additional adjustability and, what is equally, if not, more important, greater surgical exposure where needed by affixing each upper jaw engaging member to the medial end of its superior arcuate support bar and mounting the latter in a longitudinal diametric slot formed adjacent to the upper end of the post for sliding therein in a lateral and medial direction to effect positioning of the jaw engaging member and eliminate all obstruction medial thereto. A thumb screw operates in a threaded axial bore of the post and has the finger actuated head thereof projecting coaxially above the post for easy yet unobtrusive access providing means for locking the superior bar in a desired position. Each superior bar may be of a length sufficient to position the jaw engaging member along the medial line of the patient's head to oppose the tongue retractor in perfect alignment for a balanced two point suspension, the other superior bar and post being removable for complete exposure on one side of the mouth. In several modified refinements, each jaw engaging member is hinged to the medial end of its support bar for pivoting on an axis perpendicular to the length of the bar to provide movement and adjustability in the angular relation to the jaw engaging member with its support bar. The hinges incorporate spring means providing a preset tightness of pivot action or a capability for selectively varying such tightness.

The scope of the invention also contemplates an alternative form of inferior transverse bar with tongue retractor mounting means wherein laterally adjustable mandibular retractors in the form of a pair of jaw engaging members are slidably and removably mounted on the inferior transverse bar to coact with the alveolar retractors and operatively mount the mouth gag independently of the tongue retractor. The tongue retractor mounting means includes a slideway having a front wall formed with a central cutout extending the entire length thereof sized to coact with and receive therethrough a reduced width portion of the flat elongated handle of the tongue retractor in the mounting and dismounting of the latter for its detent controlled adjustability in the slideway while the mouth gag is in position on the patient. A longitudinal edge of the handle is formed with a series of spaced notches which are selectively engaged by a detent formed as a free end of a leaf spring mounted along one side of the slideway in a normally notch-engaging position and adapted to be flexed by the curved surface provided as one sidewall of each notch to permit one-way downward movement of the tongue retractor and also to be flexed completely out of said engagement to release the tongue retractor for two-way movement by a plunger positioned behind the slideway and having a head extending from the opposite side of the slideway accessible for finger pressure to effect said release.

BRIEF DESCRIPTION OF THE DRAWINGS

FIG. 14 is a front elevational view of an alternative form of mouth gag having mandibular retractors coacting with the alveolar retractors and freeing the tongue retractor from the jaw opening function, the tongue retractor being removably mountable from the front while the instrument is in position between the patient's jaws.

FIGS. 15 and 16 are sectional views taken on lines 15—15, and 16—16, respectively, in FIG. 14 showing details of the slidable and removable mounting of a mandibular retractor on the inferior transverse bar.

FIG. 17 is an enlarged fragmentary front elevational view of the tongue retractor and its removable and detent adjustable mounting in the slideway of the inferior transverse bar shown in FIG. 14, parts being broken away to show details of construction.

FIG. 18 is an enlarged sectional view taken on line 18—18 in FIG. 17 showing details of the finger pressure operable detent means for adjustably positioning the tongue retractor in the slideway.

FIG. 19 is an enlarged fragmentary perspective view of the medial end of the supporting superior bar shown in FIG. 14 illustrating another modified form of hinge construction with adjustable tensioning means and a jaw engaging member having a double beveled contact element for non-slip engagement between the teeth.

FIG. 20 is a sectional view taken on line 20—20 in FIG. 19 showing details of the adjustable tensioning means for the hinge of the jaw engaging member, and FIG. 21 is a sectional view taken on line 21—21 in FIG. 19 showing the double bevel of the jaw engaging member contact element.

DESCRIPTION OF THE PREFERRED EMBODIMENTS

Figures 1, 2:
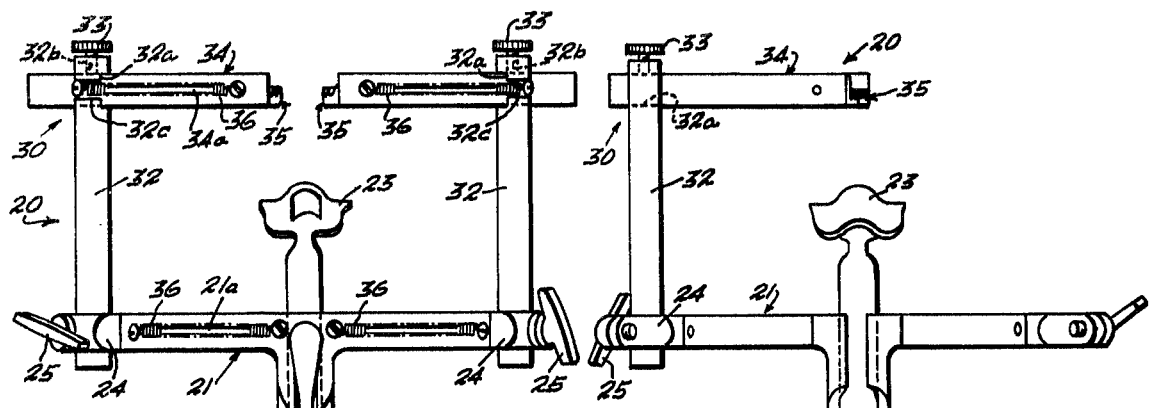
FIG. 1 is a front elevational view of the mouth gag embodying the invention showing the bilateral alveolar retractors symmetrically positioned with the lateral posts substantially fully extended and the superior bars, which terminate in jaw engaging members, in a medially extended position.
FIG. 2 is a rear elevational view of the mouth gag in FIG. 1, but showing a unilateral alveolar retractor with the superior bar in full medial extension to oppose the tongue retractor for balanced two point suspension.
Figure 3:
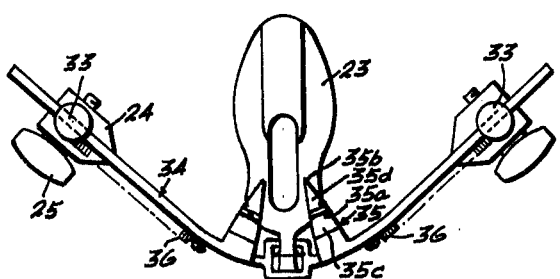
FIG. 3 is a top plan view of the mouth gag shown in FIG. 1.

Referring in detail to the drawings, 20 generally denotes a jaw retractor, also known as a mouth gag, constructed to embody the invention, seen in FIGS. 1, 2 and 3 to comprise an inferior transverse support bar 21 of arcuate configuration, that is, bowed to approximate an average contour of the face at about the level of the lower lip and of a length in excess of the width of an open mouth. Inferior support bar 21 terminates at opposite ends in split collars forming clamps 24 in which posts 32 of alveolar retractors 30 are adjustably mounted for both rotation therein and sliding movement therethrough. Each clamp 24 is provided with a thumb screw 25 for adjusting the clamping pressure applied to post 32 in the well understood manner.

Midway between clamps 24 and positioned to normally extend along the midline of the face, inferior support bar 21 is formed with a slideway 22 in which handle portion 23a of tongue retractor 23 is removably and adjustably mounted. Ratchet or detent means 22a is normally spring pressed into cooperative engagement in one of the transverse notches 23b formed in spaced relation along handle portion 23a for permitting unidirectional incremental downward movement of tongue retractor 23, as is well known in the art. Finger pressure on detent means 22a disengages the latter from the notches 23b and releases tongue retractor 23 for movement in both upward or downward directions.

Figure 9:
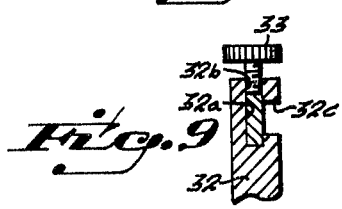
FIG. 9 is a sectional view taken on line 9—9 in FIG. 4 showing details of the slidable mounting of the superior bar in the post.

Alveolar retractors 30, except for being mirror images of each other, are structurally identical so that a description of either side applies to the other and corresponding parts are given the same reference numerals. Each alveolar retractor 30 is seen to comprise a cylindrically shaped laterally positioned post 32 having a longitudinal, diametric slot 32a located adjacent the upper end thereof in which superior arcuate bar 34 is slidably mounted for selectively positioning jaw engaging member 35, which terminates the medial end thereof, along a medial-lateral axis. Superior bar 34 is rectangular in cross-section having its larger dimension, or width, parallel to the length of post 32. As shown in FIG. 2, bar 34 may be of a length sufficient, when fully extended, to position jaw engaging member 35 on the midline of the face in alignment with tongue retractor 23, and, as will be clear from FIGS. 1 and 3, has an arcuate configuration corresponding to that of inferior support bar 21. Each half section of inferior bar 21 and each superior bar 34 are formed on the front facing sides thereof with longitudinally extending centralized depressions or grooves 21a and 34a, respectively, in which coil springs 36 seat and are attached at opposite ends thereof by suitable screws, coil springs 36 being well known in the art as quick attachment and release means for sutures. As will be apparent from FIGS. 1 and 9, the front facing wall of slot 32a on post 32 has a centralized cutout 32c sized to provide clearance for coiled spring 36 and associated fastening screws permitting free sliding movement of bar 34 in slot 32a.

An axial threaded bore 32b communicates the upper end of post 32 with slot 32a and receives therein the threaded stem of thumb screw 33 which releasably engages superior bar 34 for locking the latter in any selected position, thumb screw 33 being of the flat head type with knurled edges projecting slightly beyond the periphery of, and located for accessibility just above, the upper end of post 32.

One form of the invention contemplates superior bar 34 terminating in a relatively fixed integrally formed upper jaw engaging member 35 having spaced prominences 35a and 35b providing curved troughs 35c and 35d serving, respectively, as clearance for the lip and as a concave surface to engage the teeth or gum in the absence of dental structure.

Figure 4:
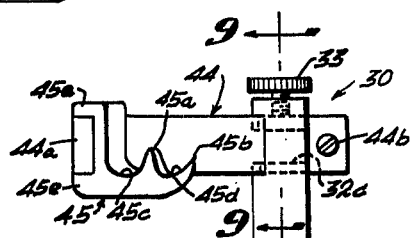
FIG. 4 is an enlarged fragmentary vertical sectional view taken through the centerline of the mouth gag in FIG. 1, but showing a modified form of alveolar retractor having a pivotally mounted jaw engaging member.
Figure 6:
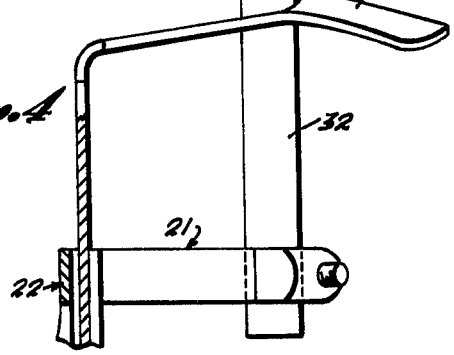
FIG. 6 is an exploded perspective view of the modified form of superior bar shown in FIG. 4.
Figure 5:
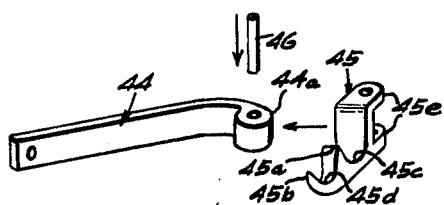
FIG. 5 is a rear perspective view of a superior bar of the alveolar retractor shown in FIG. 1 removed from the post.
Figure 7:
FIG. 7 is a vertical sectional view taken through the hinge of the superior bar shown in FIGS. 4 and 6.
Figure 8:
FIG. 8 is a fragmentary top view of the pivoted jaw engaging member of FIGS. 4, 6 and 7, an alternate adjusted position being illustrated in broken lines.
Figure 10:
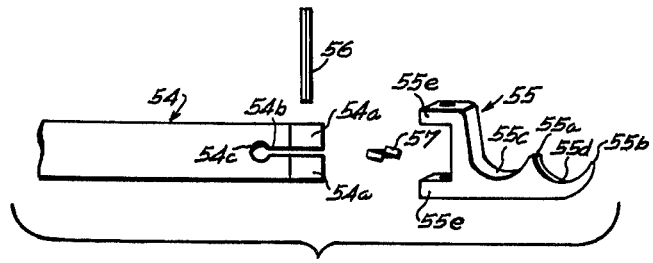
FIG. 10 is an exploded perspective view of a modified form of hinge construction for mounting the jaw engaging member under preset pivotal tension with respect to the supporting superior bar.
Figure 12:
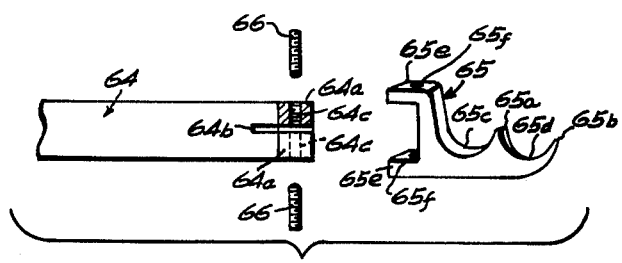
FIG. 12 is an exploded perspective view of another modified form of hinge construction for mounting the jaw engaging member under adjustable tension with respect to the supporting superior bar.

The fixed mounting of the jaw engaging member on the medial end of its superior arcuate bar, as shown in FIG. 5, may be modified to provide pivotal mounting of each jaw engaging member for adjusting the angular relation of the latter with its superior bar as will be clear from FIG. 8 to provide an optimum fit to the patient's alveolar arch as superior bar 34 is adjusted in slot 32a along its medial-lateral pathway. To this end, several forms of hinge constructions embodying the invention are shown in FIGS. 6, 10 and 12. The hinge construction of FIG. 6 is also illustrated in FIGS. 4, 7 and 8 as superior bar 44 which terminates in an integral, substantially cylindrical, enlargement 44a forming a central hinge element on which upper jaw engaging member 45 is pivoted on an axis perpendicular to the length of bar 44. Jaw engaging member 45, having spaced prominences 45a and 45b and curved troughs 45c and 45d similar to those of member 35, is also formed with spaced ears 45e, projecting as coacting hinge elements, to receive central hinge elements 44a therebetween. Hinge element 44a and ears 45e have aligned openings through which pivot pin 46 extends. Pin 46 may be a split spring, also known as a roll pin, which is compressed when assembled in the hinge to a degree for providing the required tightness between bar 44 and pivoting member 45 as hereinafter more fully described. Where desired, suitable stop means to prevent accidental disengagement of the superior bar from its post may be provided, as for example, screw 44b having its head located on the rear facing side of bar 44 adjacent the lateral end thereof, as is clear from FIG. 4.

The hinge constructions shown in FIGS. 10, 11 and 12, 13 have jaw engaging members 55 and 65 formed with prominences 55a, 55b and 65a, 65b, and troughs 55c, 55d and 65c, 65d, respectively, similar to those of members 35 and 45 and also provided with spaced ears 55e and 65e as hinge elements similar to ears 45e of member 45. Likewise, superior bars 54 and 64 are similar in configuration to bar 44 but have medial enlargements 54a and 64a providing the hinge elements formed as bifurcated structures by slots 54b and 64b, respectively, which are located centrally and extend longitudinally from the medial end laterally beyond enlargements 54a and 64a to permit slight relative movement between the bifurcated halves.

Figure 11:
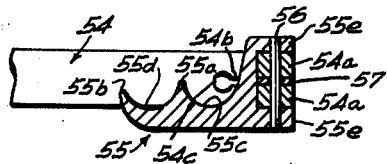
FIG. 11 is a vertical sectional view taken through the hinge showing the elements of FIG. 10 assembled.

As shown in FIGS. 10 and 11, jaw engaging member 55 is hinged to bar 54 on a suitable pin, preferably split spring pin 56, similar to pin 46, which extends through aligned openings in ears 55e and bifurcated enlargements 54a. Pin 56 also extends through lock washer 57, which is lodged in compressed condition in slot 54b. The inner end of slot 54b may be formed with an enlargement 54c to facilitate flexing of bifurcated enlargements 54a under the action of lock washer 57.

Figure 13:
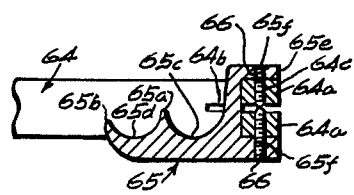
FIG. 13 is a vertical sectional view taken through the hinge showing the elements of FIG. 12 assembled.

Jaw engaging member 65 and superior arcuate bar 64 are shown in FIGS. 12 and 13 constructed to provide a hinge having means for adjusting the tension on the pivot, for locking the hinge in a desired position and for readily removably interchanging member 65. Thus, a pair of set screws 66 of uniform cross-section and having heads formed to be driven by a screw driver or Allen wrench are sized to pass through openings 65f in ears 65e to serve as a pivot pin. Each screw 66 is threaded from an opposite side into threaded opening 64c formed in each bifurcated enlargement 64a and are adapted to contact each other in the region of slot 64b.

The practical utility and operation of mouth gag 20 will now be apparent. Where three point suspension is desired, mouth gag 20 is initially assembled with bilateral alveolar retractors 30 as shown in FIG. 1, and applied to the patient's mouth in the well understood manner. Finger manipulation of thumb screws 25 loosens and tightens posts 32 for sliding movement in clamps 24 for individually adjusting the vertical separation between each superior bar 34 and inferior bar 21, and for rotational movement in clamp 24 to individually adjust the spacing of each superior bar 34 with respect to the patient's upper jaw. Likewise, finger manipulation of thumb screw 33 loosens and tightens each superior bar 34 for sliding in slot 32a in a lateral-medial direction to individually locate jaw engaging member 35 where desired along the patient's alveolar arch. These adjustments provide an effective three point suspension and enable inferior bar 21 to be properly aligned, particularly in conditions where the alveolar arch is deformed, and also render the space between the jaw engaging members 35 entirely free of obstruction for maximum surgical exposure.

It will also be apparent that each of the superior bars 44, 54 or 64, when slidably mounted in slot 32a of post 32, will not only function in a manner similar to that hereinbefore described for bars 34 in posts 32 but will also provide precise adjustability of the angular relation of each jaw engaging member 45, 55, or 65, with respect to its supporting superior bar by permitting each member 45, 55 or 65 to be properly disposed in relation to the patient's alveolar arch for achieving an optimum fit in all selected positions of bars 44, 54 or 64.

As will be clear from FIG. 7, pivotable member 45 is retained in its adjusted position by the fashioning of openings in enlargement 44a and in ears 45e so that split spring pin 46 may turn with enlargement 44a and permit movement under frictional pressure on ears 45e, or alternatively, pin 46 may turn with ears 45e and frictionally engage enlargement 44a.

FIGS. 10 and 11 illustrate a hinge construction providing greater tightness between jaw engaging member 55 and bar 54 than that afforded by the hinge construction shown in FIGS. 6 and 7 for use where such tightness, that is greater resistence to displacement of the jaw engaging member from an adjusted position, is desired. Lock washer 57, by exerting a predetermined force separating the halves of bifurcated enlargements 54a, provides friction between the latter and ears 55e augmenting the friction provided by split spring pin 56 and also compensates for wear on the friction surfaces ensuring a longer serviceable life. It will also be understood that an ordinary or solid pin (not shown) may be used in place of split spring pin 56, in which case the action of lock washer 57 is solely relied on to provide the predetermined tightness to the hinge.

The hinge construction shown in FIGS. 12 and 13 permits tightening of either of the set screws 66 to bring pressure against the opposite set screw at the abutting bottom ends thereof causing the bifurcated enlargements 64a to spread apart and thereby increase the friction applied to ears 65e. This provides adjustment for a wide range of tension from a loose pivot condition to a very tight pivot action and ultimately to locking engagement. The removal of both set screws 66 permits easy dismounting of jaw engaging member 65 from enlargements 64a and provides for an interchange of such members having prominences 65a, 65b and troughs 65c, 65d of different sizes and configurations. Where the interchangeability feature is not desired, one of the set screws 66 may be replaced by a pin (not shown) which is free of opening 65f for pivoting but is press fitted into opening 64c to abut the remaining set screw 66 which will provide the tension and locking adjustability.

An alternative construction of mouth gag is shown in FIGS. 14 and 17, generally designated 70, seen to comprise an inferior transverse bar 71 supporting alveolar retractors 30, mandibular engaging members 75 and tongue retractor 76. The inferior transverse support bar 71 is similar to support bar 21 of mouth gag 20 in respect to the curved configuration thereof, in having its opposite ends formed with clamps 74 and thumb screws 74a adjustably mounting posts 32 and in grooves with seat coil springs 36.

To serve as a mandibular retractor, inferior transverse support bar 71 mounts bilateral mandibular engaging members 75 for sliding adjustability between central slideway 72 for tongue retractor handle 77 and heads of screws 71a which project from the rear side of bar 71 located just medially of reduced width portions 71b, as shown in FIG. 16.

Each mandibular engaging member 75 has an angular configuration providing an attachment portion formed with a transverse slot 75e through which bar 71 extends. The outer wall of slot 75e has a central opening or cutout 75f which is sized to accommodate coil spring 36 and the opposite end attachment screws thereof and also to permit passage therethrough of reduced width portion 71b for removably mounting member 75 on bar 71 when screw 71a is removed to permit member 75 to slide into register with portion 71b. The jaw contacting portion of member 75 which extends at right angles to slot 75e is formed with spaced prominences 75a, 75b and with curved troughs 75c, 75d.

The coacting structure of slideway 72 and tongue retractor 76, which enables the latter to be mounted and dismounted from the front of mouth gag 70 while in operative position on the patient, is shown in FIGS. 17 and 18. Tongue retractor 76 has an elongated flat handle 77 terminating at the upper end in a rearwardly bent tongue blade 78 of conventional construction, as for example, having a central opening 78a and a channel 78b for receiving a tracheal tube (not shown) therethrough. Handle 77 has an upper portion adjacent tongue blade 78 sized to slidingly fit the track portion of slideway 72 into which access is had through a centralized cutout 72a in the front wall extending the entire length of slideway 72 between opposite side flanges 72b. A reduced width portion 77a, formed in the lower part of handle 77, is sized to pass through cutout 72a when brought into register therewith in the manner hereinafter more fully described.

Detent means, provided for controlling unidirectional sliding adjustability for tongue retractor 76 in slideway 72, is seen to comprise a leaf spring 73 mounted in an elongated depression 72c formed in a sidewall of slideway 72 to taper downwardly and inwardly creating an opening 72d communicating the lower portion of depression 72c with the track of slideway 72. A screw 73c fastens the upper end of leaf spring 73 in position in elongated depression 72c to project the inwardly curved free end 73b thereof through opening 72d to normally engage speced notches 77b which are located along an edge of handle reduced width portion 77a. Notches 77b are best seen in FIG. 17 as having a cam surface for flexing leaf spring 73 to permit downward movement of handle 77 and an opposite flat angular surface for engagement by spring end 73b to prevent upward movement of handle 77. Finger pressure responsive means for disabling the detent comprises plunger 73c disposed in a transverse bore 72f formed in slideway rear wall 72e to extend from elongated depression 72c to a small depression 72h formed in the opposite sidewall of slideway 72 to accommodate head 73e which terminates the opposite end of plunger 73c and is threaded onto a reduced diameter extension 73d which projects through a constricted end 72g of transverse bore 72f. Leaf spring 73 in its normal notch engaging position retains plunger 73c against the inner end of bore 72f thereby projecting plunger extension 73d and head by 73e beyond depression 73h. Finger pressure inwardly exerted on head 73e against leaf spring 73 flexes the latter to disengage curved free end 73b from notches 77b releasing handle 77 for free two-way sliding movement in slideway 72. To reduce the weight and conserve material, a large central opening 72j may be provided in rear wall 72e of slideway 72.

Mouth gag 70, shown in FIG. 14, adjustably mounts in clamps 74 alveolar retractors which are identical to alveolar retractors 30 in mouth gag 20, and are therefore similarly designated 30. Such similarity relates to posts 32 formed at the upper ends thereof with diametric slots 32a having cutouts 32c for sliding adjustable support therein of suitable superior arcuate bars terminating at the medial ends thereof in jaw engaging members, which bars are locked in selected position by thumb screws 33 disposed in axial threaded bores 32b.

Superior arcuate bar 84, shown in FIGS. 14, 19 and 20, is interchangeable in slot 32a with any of the superior bars 34, 44, 54 or 64 for use in both mouth gags 20 and 70 and has a pivotal mounting for jaw engaging member 85 formed as medial enlargements 84a bifurcated by slot 84b. Jaw engaging member 85 may be pivoted by spaced ears 85e and 85f to medial enlargements 84a by any suitable pivot pin passing through openings therein, such as, split spring pin 86 and is formed with prominences 85a, 85b and troughs 85c, 85d. As another modification of means for adjusting the tension on the hinge between medial enlargements 84a and ears 85e, 85f, slot 84b, along a midportion thereof, has threaded tapered opening 84c receiving therein a similarly tapered screw 84d which when tightened will spread medial enlargements 84a apart exerting pressure on ears 85e, 85f.

In order to improve the grip on the teeth by the alveolar and mandibular retractors and prevent sidewise shifting, the trough which engages the teeth, namely, trough 85d in jaw engaging member 85, has double bevel surfaces 85g to provide a wedge-shaped cross-section with a relatively thin edge to lodge between any two adjacent teeth. Trough 75d of of mandibular engaging member 75 is also illustrated in FIGS. 15 and 16 as having similar beveled surfaces. Where desired troughs 35d, 45d, 55d and 65d of jaw engaging members 35, 45, 55 and 65, respectively, may likewise be provided with the double bevel construction. The thin edge of trough 85d is sufficiently blunt so that, where gum contact is required due to absence of teeth, the wedge-shaped contour will create a depression in the gum to reduce the sidewise shifting without cutting into the tissue.

Assembly of slideway 72 with the separate parts of the detent means, namely, leaf spring 73, fastening screw 73a, plunger 73c and head 73e, is performed by first inserting threaded end 73d through sidewall depression 72c and then into and through bores 72f, 72g to extend beyond depression 72h for threading head 73e thereon. Thereafter leaf spring 73 is secured in position in depression 72c by screw 73a so that curved end 73b extends through opening 72d for operative engagement with notches 77b when handle reduced width portion 77a is located in the track of slideway 72.

Mouth gag 70 is intended to be initially mounted between the jaws of the patient with tongue retractor 76 removed from slideway 72, which removal is readily accomplished by applying finger pressure to head 73e of plunger 71 thereby releasing handle 77 for upward movement in slideway 72 until the upper full width portion of handle 77 clears the upper end of slideway 72 to register reduced width portion 77a with the entire length of centralized cutout 72a for passage therethrough as will be clear from FIG. 17. Then, after mouth gag 70 is mounted on the patient by jaw contact of the alveolar and mandibular retractors utilizing the sliding adjustability of mandibular engaging members 75 along inferior transverse bar 71, the sliding and rotational adjustability of posts 30 in clamps 74, the sliding adjustability of a selected superior arcuate bar 44, 54, 64 or 84 in slots 32a and the pivotal adjustability of a selected jaw engaging member 45, 55, 65 or 85, tongue retractor 76 may then be mounted in slideway 72 by bringing reduced width portion 77a of handle 77 into registered alignment with centralized cutout 72a so as to pass therethrough into the track and then moving handle 77 downwardly so that the full width portion enters the track and is retained therein by opposite side flanges 72b. Handle 77 may now be adjusted downwardly by pressure applied at finger grip 77c for proper positioning of the patient's tongue. Finger pressure on head 73e releases handle 77a for upward adjustment when required and for removal of handle 77 as hereinbefore described.

Where a two point suspension is indicated, as when maximum exposure on one side of the mouth is desired, post 32 on the work area side is removed from clamp 24 and superior bar 34 on the opposite side is fully extended to position jaw engaging member 35 at the midline of the head in alignment with tongue retractor 23, as is clear from FIG. 2. Likewise, utilizing mouth gag 70, a single alveolar retractor with jaw engaging member in midline alignment may be used coacting with the pair of mandibular retractors 75.

The jaw retractor instruments, or mouth gags, herein disclosed are seen to achieve the several objects of the invention and to be well adapted to meet conditions of practical use. As various possible embodiments might be made of this invention, and as various changes might be made in the disclosed instruments, it is to be understood that all matters herein set forth or shown in the accompanying drawings are to be interpreted as illustrative and not in a limiting sense.

What is claimed is:

1. In a jaw retractor instrument, an inferior transverse arcuate support bar sized and shaped to conform to the face at about the level of the lips, a tongue retractor slideway centrally located on said inferior bar extending at right angles thereto, a clamp terminating each opposite end of said inferior bar, an alveolar retractor comprising a cylindrical post adjustably and removably supported in each of said clamps, each of said posts having a diametric slot located adjacent the upper end thereof, a superior arcuate bar slidably mounted in said slot and terminating at a medial end thereof in an upper jaw engaging member for selective positioning along the alveolus of the patient by said superior bar slidability, and a thumb screw threaded into said post releasably engaging and locking said superior bar in said selected position in said slot.

2. The jaw retractor instrument defined in claim 1, in which said post has an axially extending threaded bore communicating the upper end of the post with said slot and said thumb screw is threaded in said bore.

3. The jaw retractor instrument defined in claim 1, in which a coiled spring is mounted on the front facing side of said superior bar and a front facing wall of said slot has the central portion thereof cutout as clearance for the spring to permit said sliding movement of the superior bar in the slot.

4. The jaw retractor instrument defined in claim 1, a tongue retractor having an elongated handle terminating at an upper end in an angularly disposed tongue blade, said handle being removably and slidably mounted in said slideway for adjustment of said blade with respect to said inferior bar, said superior arcuate bar being of a length sufficient to position said upper jaw engaging member at the medial line of the patient's face and in alignment with said tongue retractor providing a two-point balanced suspension for the instrument.

5. The jaw retractor instrument defined in claim 1, in which said upper jaw engaging member is pivotally mounted on said superior arcuate bar medial end on an axis perpendicular to the length of the bar for angular adjustment to said alveolus for optimum engagement therewith.

6. In an alveolar retractor of a jaw retractor instrument, a lateral support post having an upper end, a superior arcuate bar terminating at a medial end thereof in an upper jaw engaging member, said bar being slidably mounted in the upper end of said support post for selectively positioning said jaw engaging member along the alveolar arch of the patient, said jaw engaging member being pivotally mounted at said superior bar medial end on an axis perpendicular to the length of the bar for angular adjustment to said alveolar arch for optimum engagement therewith, and means for controlling the tension on said pivotal mounting.

7. The alveolar retractor defined in claim 6, in which said pivotal mounting and means for controlling the tension thereon includes an enlargement on said medial end of said superior arcuate bar, a slot through said superior arcuate bar located centrally and extending longitudinally from the medial end laterally beyond said enlargement dividing the latter into bifurcated halves, said jaw engaging member having a pair of ears spaced for receiving said bifurcated enlargement therebetween, aligned openings in said bifurcated enlargement and ears, a pivot pin extending through said openings, and pressure exerting means applied to separate said halves of the enlargement to apply a friction pressure between the enlargement and said ears of the jaw engaging member.

8. The alveolar retractor defined in claim 7, in which said pressure exerting means includes a lock washer on said pivot pin in compressed condition in said slot.

9. The alveolar retractor defined in claim 7, in which said pressure exerting means includes said pivot pin as a pair of set screws, said ear openings being sized for pivoting on said set screws, said openings in each of said enlargement halves being threaded to receive one of said set screws in opposite directions to abut at the bottom ends thereof at said slot whereby tightening of one of said screws against the other provides adjustability of said friction pressure from a relative looseness to a locking tightness and removal of said set screws provides for interchangeability of jaw engaging members.

10. The alveolar retractor defined in claim 7, in which said pressure exerting means includes a tapered threaded opening formed in a midportion of said slot, and an adjustable tapered screw engaged in said threaded opening.

11. In a jaw retractor instrument, an inferior transverse arcuate support bar sized and shaped to conform to the face at about the level of the lips, a tongue retractor slideway centrally located and rigidly formed on said inferior bar extending at right angles thereto in an inferior-superior direction and having a longitudinal front opening, means located at each opposite end of said inferior bar adjustably supporting an alveolar retractor having laterally adjustable upper jaw engaging members, a pair of mandibular retractors mounted for lateral adjustability on said inferior bar, one of said pair of mandibular retractors being located on each side of said slideway, a tongue retractor having an elongated handle slidingly engaging said slideway and terminating at an upper end in an angularly disposed tongue blade, said handle having a portion of reduced width for passing through said slideway front opening for removal and replacement of the tongue retractor while said instrument is mounted on the patient's mouth by upper and lower jaw engagement of said alveolar and mandibular retractors.

12. The jaw retractor instrument defined in claim 11, in which each of said mandibular retractors has an angular configuration providing an attachment portion formed with a transverse slot through which said inferior bar extends, an outer wall of said slot having a central opening, said inferior bar having a reduced width portion adjacent said alveolar retractor supporting means sized and shaped to fit through said central opening when said mandibular retractor is in registered alignment therewith, and removable screw stop means on said inferior bar normally preventing said registered alignment.

13. In a jaw retractor instrument, an inferior transverse arcuate support bar, a tongue retractor slideway (medially) centrally located on said bar extending at right angles thereto and comprising a pair of opposite sidewalls, a front wall and a rear wall defining a track in said slideway, a tongue retractor having an elongated handle terminating at an upper end in an angularly disposed tongue blade, said tongue retractor handle having an upper portion adjacent the tongue blade being of a width to slidingly engage (a) said track (in said slideway), a lower portion of said handle being of reduced width formed by a cutback along one longitudinal edge, the opposite edge having a detent engaging portion formed as spaced notches, said slideway (track having a) front wall being formed with a centralized cutout extending the entire length of the track for removably mounting said handle therethrough, the width of the cutout approximating that of (the) said handle reduced width portion for passage of the latter therethrough when fully in register therewith, and pressure operated detent means having a detent element extending through an opening in one of said sidewalls (the sidewall of said slideway) communicating with said track normally selectively engaging one of said spaced notches for unidirectional downward adjustability of the tongue retractor.

14. The jaw retractor instrument defined in claim 13, in which said detent means includes an elongated depression formed in said slideway sidewall tapering downwardly and inwardly creating said opening to said track, and a leaf spring mounted in said depression having a free end normally extending through said opening as said detent element, a plunger extending through a transverse bore formed in said rear wall of the slideway communicating with said elongated depression, said plunger contacting a midportion of said spring and having a free end extending from an opposite side of said slideway for application of finger pressure to disengage said spring from said notches for freeing said handle for two-way sliding movement in said track.

15. In a jaw retractor instrument, an alveolar retractor comprising a lateral post having an upper end and a supporting bar having a jaw engaging member terminating a medial end thereof, said supporting bar being mounted in said post upper end for sliding adjustability along a path for selectively positioning said jaw engaging member along the alveolus of the patient, said jaw engaging member having one end thereof pivoted to said supporting bar medial end on an axis perpendicular to said path for angular adjustment to said alveolus and an opposite free end for projecting into the mouth of the patient, said jaw engaging member having two spaced prominences and two curved troughs in tandem relation, a first of said prominences being located at said opposite free end, a first of said troughs being located between said prominences to engage the teeth, the other trough being formed inwardly of said free end and beyond the second prominence serving as clearance for the lip, said first trough having double beveled side surfaces providing a wedge-shaped cross-section with a relatively thin edge to lodge between any two adjacent teeth and prevent sidewise shifting of the member along said alveolus.

* * * * *